United States Patent
Noblitt

(10) Patent No.: US 12,232,962 B2
(45) Date of Patent: Feb. 25, 2025

(54) METHODS AND DEVICES TO REDUCE THE RISK OF INFECTION

(71) Applicant: Armis Biopharma, Inc., Fort Collins, CO (US)

(72) Inventor: Scott Noblitt, Fort Collins, CO (US)

(73) Assignee: ARMIS BIOPHARMA, INC., Fort Collins, CO (US)

( * ) Notice: Subject to any disclaimer, the term of this patent is extended or adjusted under 35 U.S.C. 154(b) by 781 days.

(21) Appl. No.: 16/780,581

(22) Filed: Feb. 3, 2020

(65) Prior Publication Data

US 2020/0246511 A1  Aug. 6, 2020

Related U.S. Application Data

(60) Provisional application No. 62/800,702, filed on Feb. 4, 2019.

(51) Int. Cl.
| | |
|---|---|
| A61F 2/28 | (2006.01) |
| A61L 24/00 | (2006.01) |
| A61L 24/02 | (2006.01) |
| A61L 27/04 | (2006.01) |
| A61L 27/30 | (2006.01) |
| A61L 27/54 | (2006.01) |
| A61L 27/58 | (2006.01) |

(Continued)

(52) U.S. Cl.
CPC ............ *A61F 2/28* (2013.01); *A61L 24/0015* (2013.01); *A61L 24/0042* (2013.01); *A61L 24/02* (2013.01); *A61L 27/047* (2013.01); *A61L 27/306* (2013.01); *A61L 27/54* (2013.01); *A61L 27/58* (2013.01); *A61L 31/022* (2013.01); *A61L 31/088* (2013.01); *A61L 31/148* (2013.01); *A61L 31/16* (2013.01); *A61F 2002/30062* (2013.01); *A61L 2300/404* (2013.01); *A61L 2420/02* (2013.01); *A61L 2420/06* (2013.01); *A61M 1/92* (2021.05)

(58) Field of Classification Search
CPC ............. B05C 17/0212; B05C 17/0242; A61L 2430/02; A61F 2002/30797
See application file for complete search history.

(56) References Cited

U.S. PATENT DOCUMENTS

| | | | |
|---|---|---|---|
| 5,376,120 A | * | 12/1994 | Sarver ..................... F24V 30/00 623/23.58 |
| 5,423,859 A | | 6/1995 | Koyfman et al. |

(Continued)

FOREIGN PATENT DOCUMENTS

| | | |
|---|---|---|
| EP | 1663333 B1 | 11/2018 |
| WO | 2019010465 | 1/2019 |

OTHER PUBLICATIONS

Sriprapha et al., A Study of Mechanical Properties of Bone Cement Containing Micro- and Nano-Hydroxyapatite Particles, Apr. 13, 2018, Key Engineering Materials, vol. 766, pp. 117-121 (Year: 2018).*

(Continued)

*Primary Examiner* — Dah-Wei D. Yuan
*Assistant Examiner* — Andrew J Bowman
(74) *Attorney, Agent, or Firm* — Fox Rothschild LLP

(57) ABSTRACT

Articles for reducing the risk of infection, bearing, or containing an antimicrobial composition containing a solid-phase peroxyxcarboxylic acid metal salt are provided. Methods of reducing the risk of infection using the antimicrobial composition are also provided.

9 Claims, 2 Drawing Sheets

Figure 1:
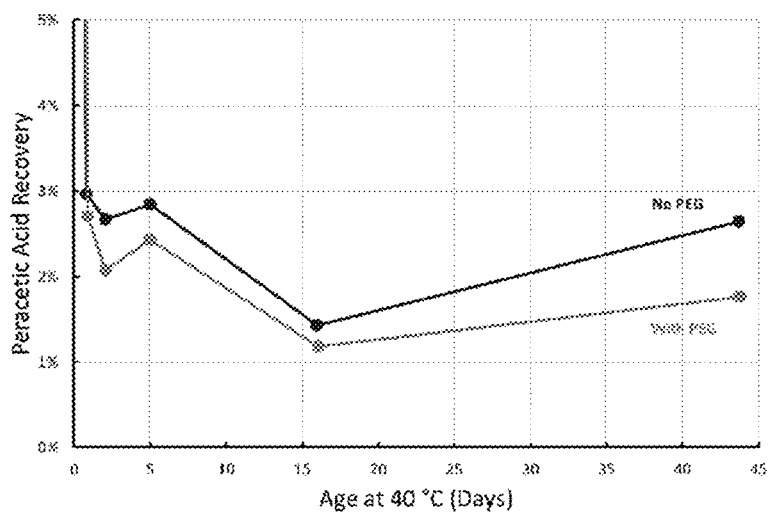

(51) Int. Cl.
*A61L 31/02* (2006.01)
*A61L 31/08* (2006.01)
*A61L 31/14* (2006.01)
*A61L 31/16* (2006.01)
*A61F 2/30* (2006.01)
*A61M 1/00* (2006.01)

(56) References Cited

U.S. PATENT DOCUMENTS 9,427,417 B2 8/2016 Myntti
2018/0000984 A1* 1/2018 Vogt ................. C08L 33/12

OTHER PUBLICATIONS

Mei, et al., J. Chem. Eng. Data (1995), 40 pp. 1168-1171.
International Search Report and Written Opinion dated Apr. 16, 2020 in Application PCT/US2020/016432.

* cited by examiner

METHODS AND DEVICES TO REDUCE THE RISK OF INFECTION

RELATED APPLICATIONS AND CLAIM OF PRIORITY

This patent document claims priority to U.S. Provisional Patent Application No. 62/800,702, filed Feb. 4, 2019, the disclosure of which is fully incorporated into this document by reference.

FIELD OF THE INVENTION

The present invention relates to methods and devices to reduce the risk of infection using an antimicrobial solid-phase peroxyxcarboxylic acid metal salt composition.

BACKGROUND OF THE INVENTION

One of the major problems encountered in a medical setting is the risk of the patient developing an infection. There exist different treatments for patients who have developed infections, such as, for example, antibiotics. However, antibiotic resistance is rising, leading to higher medical costs, prolonged hospital stays, and increased mortality. Antimicrobial resistance, generally, has become a global crisis, resulting in approximately 700,000 deaths annually. Over time, bacteria develop new resistance mechanisms, which inhibit the ability of medical professionals to treat even common infectious diseases. As a result, the list of infections that are becoming harder, or sometimes impossible, to treat is growing. Estimates are that this crisis could grow to 10 million deaths and $100 trillion in costs by 2050.

Surgery inherently comes with a relatively high risk of infection. Medical personnel take great precaution, and have extensive protocols to prevent infection of patients, however, despite their efforts, any surgery that causes a break in the skin may still lead to a surgical site infection (SSI). Typical surgical site infections include superficial incisional SSI, occurring in the area of skin near the incision; deep incisional SSI, occurring in the muscles and tissue beneath the incision area; and organ or space SSI, occurring in an area of the body other than skin, muscle, and surrounding tissue that was involved in the surgery, such as body organs or the space between organs. Post-surgery infections are caused by microbes, usually the bacteria *Staphylococcus*, *Streptococcus*, and *Pseudomonas*. Microbes can infect a surgical wound through various forms of contact, such as from a contaminated person or surgical instrument, through microbes in the air, or through microbes that are already on or in the patient's body and then spread into the wound. Surgical site infections may cause relatively mild symptoms such as pus or drainage, fever or chills, or pain. While the majority of surgical site infections resolve with treatment, they can have devastating consequences for patients, including death.

The risk of infection for patients undergoing medical implantation surgery is high. Medical implants have been in use in medicine for a long time to support or substitute for body functions. In particular, defective joints of the body are replaced by articular implants with increasing success, which often is associated with a substantial improvement in the quality of life of the patient. However, an implant-induced infection is still one of the most dreaded complications of the procedure, and constitutes the principal cause of revision surgery, with more than 30,000 orthopedic implant revision surgeries being performed each year. This type of infection can be extremely difficult to treat. Bacteria such as staphylococci, bind to the implant and the surrounding damaged tissue, and form biofilms that may mature after a few days. Where the infection persists for more than about 10 days, complications such as bone necrosis, which may result in the collapse of the architecture of bone, and chronic osteomyelitis, which are characterized by the persistence of micro-organisms on the dead bone and implant, may occur. The implant and dead bone must usually be removed to achieve a cure, which typically requires the use of strong intravenous antibiotics. The implant is usually not replaced until clinical findings and laboratory parameters have returned to normal. This entire process disadvantageously involves an extended hospital stay, high costs, delayed mobilization and rehabilitation, placing significant strain on the patient, physician and healthcare system. Typical procedures for attempting to avoid these infections in the first place include decontaminating instrument sets, debridement to remove materials that may promote infection and impede healing, use of culture directed antibiotics and delivery of local antibiotics, and cleansing the surgical wound and implants with liquid antiseptics. However, as evidenced by the number of revision surgeries necessitated due to infection, these procedures are not foolproof.

It is already known from the prior art that implant surfaces need to be modified for an optimum integration of the implants in the surrounding body tissue. For example, cemented articular endoprostheses utilize a fast-drying bone cement to help affix the prosthesis to the bone. However, the cement may break down, causing the artificial joint to come loose, prompting the need for revision surgery, or the cement debris may irritate the surrounding soft tissue, causing inflammation. Non-cemented articular endoprostheses, which are often preferred, usually have a roughened (often sand-blasted) or textured porous surface, which is designed to improve the integration of the bone tissue. Attempts have been made to modify the implant surface to enhance bone anchorage and improve implant biocompatibility. The various methods previously attempted have some disadvantages, such as poor adhesion to the implant substrate and heterogenous composition. There is a great interest in configuring the implant surfaces to not only promote osseointegration, but also deter bacterial adhesion and minimize prosthetic infection. Antimicrobial or antibiotic agents are widely used to treat, as well as to prevent infection. Different types of implant surface coatings containing silver, copper, zinc, chlorhexidine, and antibiotics like gentamycin, cephalothin and amoxicillin, have been tried to provide antimicrobial properties to orthopedic implants. However, these methods have some disadvantage, such as difficulty in controlling and distributing the release of the agent, as well as the difficulty in maintaining a therapeutically relevant concentration of the agent in an appropriate body region. Thus, there remains a need for implants that prevent or reduce the risk of development of infections associated with implant procedures, and that preferably also promote osseointegration.

Likewise, there remains a need for new methods and devices for minimizing the risk of infections, generally, both within and outside of medical procedures. In particular, there remains a need for new methods and devices that are effective against microbes, and have a mechanism of action against the microbes, for which the microbes cannot develop resistance. Further, there is a need for such antimicrobial treatments to be robust enough to maintain their effectiveness over extended periods of time when applied to surfaces.

SUMMARY OF THE INVENTION

The present invention relates to articles and methods to reduce the risk of infection using an antimicrobial solid-phase peroxyxcarboxylic acid metal salt.

Accordingly, in a first aspect of the invention, there is provided an article configured for tissue contact, comprising a surface onto which is applied or through which is absorbed an antimicrobial composition, comprising a solid-phase peroxyxcarboxylic acid metal salt, said metal salt comprising a reaction product of a mixture, comprising hydrogen peroxide, a peroxycarboxylic acid and a basic metal salt selected from the group consisting of a magnesium, zinc or lithium metal salt.

In one embodiment of the invention, the antimicrobial composition further comprises acetic acid. In a different embodiment, the molar ratio of peroxycarboxylic acid to basic metal salt in the mixture is from about 0.1:1 to about 10:1. In another embodiment of the invention, the amount of peroxycarboxylic acid in the antimicrobial composition is from 0.1% to 85%. In yet another embodiment of the invention, the peroxycarboxylic acid is selected from the group consisting of peracetic acid, performic acid, percitramalic acid, permaleic acid percitraconic acid, perpropionic acid, perbutyric acid, perisobutyric acid, perglutaric acid, persuccinic acid, permalonic acid, perbenzoic acid, perphthalic acid, perlactic acid, perglycolic acid, or a combination thereof. In a different embodiment of the invention, the basic metal salt is selected from the group consisting of a carbonate, hydroxide, oxide, acetate or formate metal salt, or a metal salt of an organic acid corresponding to the reduced form of the peroxycarboxylic acid, or a combination thereof. In a further embodiment of the invention, the antimicrobial composition is applied at a thickness of at least 10 µm.

In yet a further embodiment of the invention, the article is selected from the group consisting of a wipe, bandage, cloth, surgical covering, surgical dressing, gauze, surgical sponge, or surgical drape. In still a further embodiment of the invention, the article is made of a material selected from the group consisting of woven textile fabric, nonwoven fabric, or sponge.

In one embodiment of the invention, the article is suitable for use in combination with negative pressure wound therapy. In another embodiment, the article is designed to be used to treat a target selected from the group consisting of a burn, wound, cut, or dermal lesion. In a further embodiment of the invention, the burn is selected from the group consisting of a thermal burn, sunburn, or chemical burn. In still a further embodiment, the wound is selected from the group consisting of an abrasion, incision, laceration, puncture, avulsion, amputation, or laser treatment wound. In a different embodiment, the dermal lesion is selected from the group consisting of a pressure ulcer, stasis ulcer, diabetic ulcer, decubitus ulcer, foot ulcer or venous ulcer.

In one embodiment of the invention, the antimicrobial composition is capable of treating or preventing infections of a type selected from the group consisting of bacterial, fungal, viral, or toxic infections. In another embodiment, the fungal infection is a foot or nail infection. In a different embodiment, the article is suitable for use as at least one of a topical therapeutic, surface disinfectant, or surgical disinfectant.

In one embodiment of the invention, the article is an implant. In another embodiment, the implant is selected from the group consisting of articular endoprosthesis, endosteal implant, subperiosteal implant, bone augmentation, pacemaker, defibrillator, neurostimulator, ophthalmic implant, implantable shunt, artificial joint, hip implant, knee implant, stent, implantable coil, pump, intrauterine device (IUD), heart valve, surgical fastener, surgical staple, surgical pin, surgical rod, surgical screw, implantable electrical lead, and implantable plate. In a further embodiment of the invention, the implant is an insert in a lumen of a medical device. In yet another embodiment of the invention, the insert is a cannula or cannulated screw. In still a further embodiment, the implant is made of a material selected from the group consisting of titanium, titanium alloy, ceramic, polymer, stainless steel, tantalum, gold alloy, cobalt-chromium alloy, or nickel-chromium alloy. In another embodiment, the antimicrobial composition is incorporated into at least one of a bone filler or bone cement. In a different embodiment, the antimicrobial composition is applied on the implant on top of a previously applied coating. In yet another embodiment, the implant is configured to be temporarily, semi-permanently or permanently inserted in a subject.

In one embodiment of the invention, the implant is bioabsorbable. In another embodiment, the bioabsorbable implant is useful for at least one of wound closure, tissue repair, tissue engineering, controlled delivery system, or prosthesis. In yet another embodiment, the bioabsorbable implant is selected from the group consisting of a suture, staple, adhesive, mesh, internal bone fixation device, engineered blood vessel, engineered skin, engineered bone, engineered cartilage, engineered liver, microcapsule, ion-exchange resin, string, filament and wire. In a further embodiment, the bioabsorbable implant is designed to be absorbed over a predetermined time period after insertion into a subject. In yet a further embodiment, the implant is a bioabsorbable implant that is co-implanted with a non-bioabsorbable implant. In still a further embodiment, the bioabsorbable implant at least partially covers, surrounds or holds the non-bioabsorbable implant. In a different embodiment, the bioabsorbable implant is at least one of impregnated or coated with the antimicrobial composition. In another embodiment, the implant is a bioabsorbable implant comprising an envelope, pouch, pocket, bag, net or mesh.

According to a second aspect of the invention, there is provided a method of reducing the risk of infection in subjects comprising, inserting the article in a subject.

According to a third aspect of the invention, there is provided a method of reducing the risk of infection in subjects comprising, applying to a surface or impregnating within a surface, a solid-phase peroxycarboxylic metal salt comprising a reaction product of a solution or suspension comprising hydrogen peroxide, a peroxycarboxylic acid, and a basic metal salt selected from the group consisting of a magnesium, lithium or zinc metal salt, wherein the surface is on an article configured for tissue contact, or a body tissue. In one embodiment of the invention, the solid-phase peroxycarboxylic metal salt further comprises acetic acid. In another embodiment of the invention, the method further comprises a step of implanting the medical implant in a subject in need thereof.

According to a fourth aspect of the invention, there is provided a method of reducing the risk of infection in subjects comprising: (a) forming a reaction solution or suspension by mixing hydrogen peroxide, a peroxycarboxylic acid, and a basic metal salt selected from the group consisting of a magnesium, lithium or zinc metal salt, to create a composition comprising a solid-phase peroxycarboxylic metal salt precipitate; (b) drying the composition to form a dry solid-phase peroxycarboxylic acid metal salt antimicrobial composition; and (c) at least one of applying the antimicrobial composition to, or impregnating the antimicrobial composition within, a surface, wherein the surface is on an article configured for tissue contact, or a body tissue. In one embodiment of the invention, the reaction solution or suspension is further mixed with acetic acid.

According to one embodiment of the methods of invention, the article is selected from the group consisting of a wipe, bandage, cloth, surgical covering, surgical dressing, gauze, surgical sponge, or surgical drape. According to another embodiment, the article is made of a material selected from the group consisting of woven textile fabric, nonwoven fabric, or sponge. According to yet another embodiment, the article is used in combination with negative pressure wound therapy. In another embodiment, the article is used to treat a target selected from the group consisting of a burn, wound, cut, or dermal lesion. In a further embodiment, the antimicrobial composition is capable of treating or preventing infections of a type selected from the group consisting of bacterial, fungal, viral, or toxic infections. In yet a further embodiment, the antimicrobial composition is suitable for use as at least one of a topical therapeutic, surface disinfectant, or surgical disinfectant.

In one embodiment of the methods of the invention, the article is an implant. In another embodiment, the method of the invention further comprises the step of inserting the implant in a subject. In yet another embodiment, the implant is selected from the group consisting of an articular endoprosthesis, endosteal implant, subperiosteal implant, bone augmentation, pacemaker, defibrillator, neurostimulator, ophthalmic implant, implantable shunt, artificial joint, hip implant, knee implant, stent, implantable coil, pump, intrauterine device (IUD), heart valve, surgical fastener, surgical staple, surgical pin, surgical rod, surgical screw, implantable electrical lead, and implantable plate. In still another embodiment, the implant is an insert in a lumen of a medical device. In a further embodiment, the insert is a cannula or cannulated screw. In yet a further embodiment, the implant is bioabsorbable. In a different embodiment, the implant is co-implanted with a non-bioabsorbable implant. In another embodiment, the bioabsorbable implant at least partially covers, surrounds or holds the non-bioabsorbable implant. In yet another embodiment, the implant is temporarily, semipermanently or permanently inserted in a subject.

In one embodiment of the methods of the invention, the molar ratio of peroxycarboxylic acid to basic metal salt is from about 0.1:1 to about 10:1. In another embodiment of the invention, the amount of peroxycarboxylic acid in the antimicrobial composition is from 0.1% to 85%. In yet another embodiment of the invention, the reaction solution or suspension has a pH of from 2 to 8. In a further embodiment of the invention, the basic metal salt is present in the reaction solution or suspension in an amount sufficient to achieve a pH of from 2 to 8. In still a further embodiment of the invention, the reaction solution or suspension further comprises polyethylene glycol. In a different embodiment of the invention, the amount of polyethylene glycol is from greater than 0 wt % to 75 wt %, based on the total weight of the reaction solution or suspension. In another embodiment of the invention, the peroxycarboxylic acid is selected from the group consisting of peracetic acid, peroxyformic acid, percitramalic acid, permaleic acid and percitraconic acid, perpropionic acid, perbutyric acid, perisobutyric acid, perglutaric acid, persuccinic acid, permalonic acid, perbenzoic acid, perphthalic acid, perlactic acid, perglycolic acid, or a combination thereof. In yet another embodiment of the invention, the basic metal salt is selected from the group consisting of a carbonate, hydroxide, oxide, acetate, or formate metal salt, or a metal salt of an organic acid corresponding to the reduced form of the peroxycarboxylic acid, or a combination thereof. In a further embodiment of the invention, the antimicrobial composition is applied at a thickness of at least 10 μm. In still a further embodiment of the invention, the peroxycarboxylic acid is non-cationic. In a different embodiment of the invention, the peroxycarboxylic acid is cationic, and the method includes the further step of adding a counteranion. In a further embodiment of the invention, the method further comprises a step of implanting the medical implant in a subject in need thereof. In still a further embodiment of the invention, the amount of hydrogen peroxide in the solution or suspension is from 0.01 wt % to 50 wt %, based on the total weight of the reaction solution or suspension. In another embodiment of the invention, the amount of peroxycarboxylic acid in the solution or suspension is from 0.01 wt % to 50 wt %, based on the total weight of the reaction solution or suspension.

BRIEF DESCRIPTION OF THE DRAWINGS/FIGURES

FIG. 1 represents peracetic acid recovery in Mg/antimicrobial solution compositions with and without PEG 3350, confirming that the solid-phase antimicrobial composition can be prepared without a polymer matrix support. Antimicrobial composition starting solution contained ~21 wt % antimicrobial solution and ~4.3 wt % magnesium acetate tetrahydrate. Drying and storage were done at 40° C.

Figure 2:
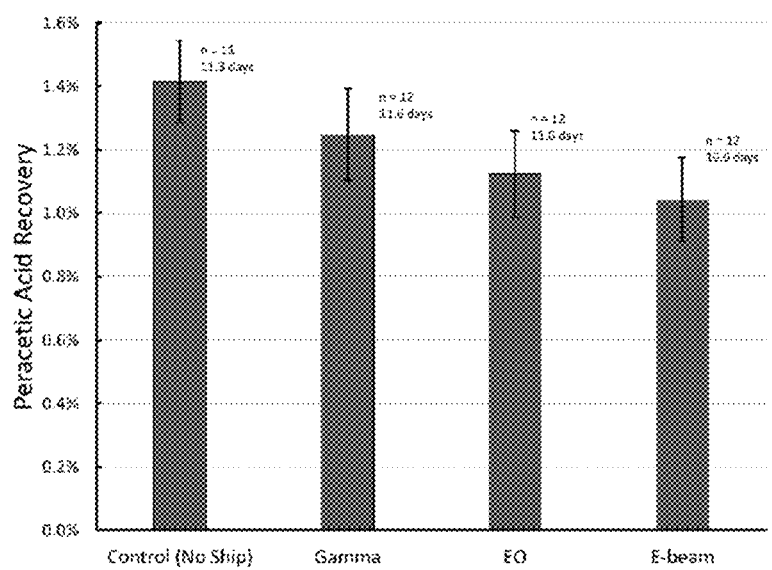

FIG. 2 represents peracetic acid recovery in Mg/PEG/antimicrobial solution compositions subjected to sterilization conditions. The "n" value is the number of replicates in each group. The time shown is the average age of the replicates, where age is considered post-oven time. Error bars are the 95% confidence intervals. All antimicrobial compositions were stored in an oven at 40° C. for 31 days before being removed, and stored in desiccated bags. The controls stayed in the lab at ambient temperature, whereas the three sterilization groups were shipped, sterilized, shipped back, then analyzed.

Figure 3:
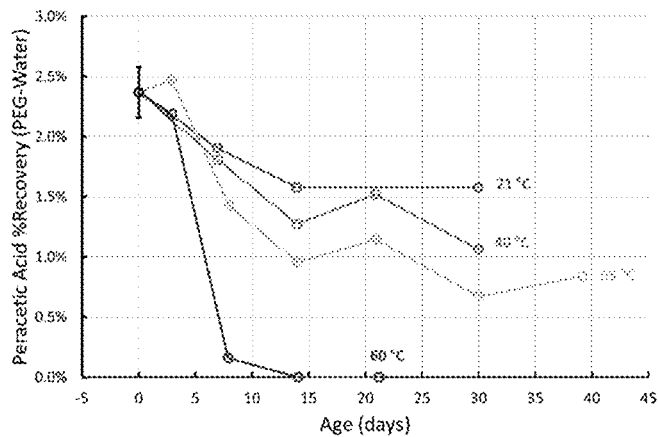
Figure 4:
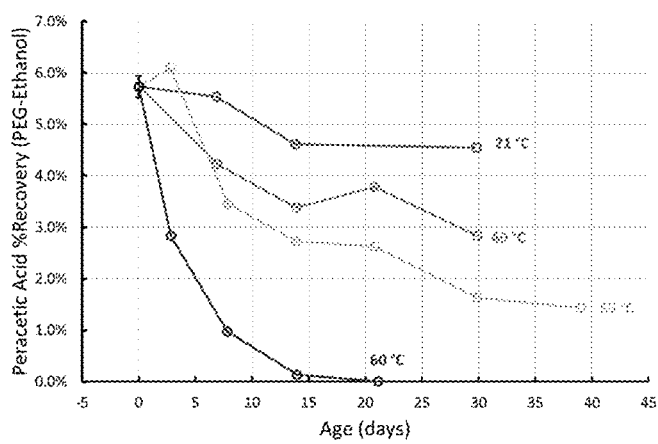

FIG. 3 and FIG. 4 represent lifetimes of antimicrobial compositions subjected to accelerated-aging tests, confirming lifetimes of six months or longer, where the antimicrobial solution was diluted with water (FIG. 3) or ethanol (FIG. 4).

DETAILED DESCRIPTION OF THE INVENTION

Unless otherwise defined, all technical and scientific terms used herein have the same meaning as commonly understood by one of ordinary skill in the art to which this invention pertains. In the case of conflict, the present document, including definitions, will be controlling.

The present invention provides articles and substrates that have been treated with a solid-phase antimicrobial composition containing a solid-phase peroxycarboxylic acid metal salt, as well as methods of reducing the risk of infection using the antimicrobial composition.

The article of the invention has a solid phase antimicrobial composition in it, or on it, or both. It may be at least partially coated with the antimicrobial composition, and/or it may have the composition absorbed or impregnated within at least a part of it. The composition has antimicrobial, disinfecting and/or wound healing properties that enable the treatment or reduction of the risk of infection in subjects. It will be understood by those skilled in the art that microbes include for example, bacteria, viruses, protozoa, and fungal organisms. The antimicrobial composition may be effective in treating or at least partially preventing infections associated with any of the different types of microbe.

The antimicrobial composition is in the solid phase, preferably in the form of a powder. The solid-phase composition provides certain advantages over liquid-phase antimicrobial treatments. One advantage associated with the present invention is that the solid-phase antimicrobial composition is easier to apply and control than a liquid-based composition. In part, this is because the solid-phase composition does not release its antimicrobial components until it comes into contact with moisture, for example from body tissue or fluid. Another advantage is that once applied, the solid-phase composition attaches to the surface of the article or substrate better than liquid compositions. Additionally, the solid form of the composition advantageously enables the slow release of the antimicrobial compounds in the composition, once the article comes into contact with the fluids and/or tissue in the subject's body. The solid-phase composition may be configured so that the release of the antimicrobial compounds within the composition (e.g., peroxycarboxylic acid) is sustained over a predetermined time period of continuous or intermittent exposure to bodily fluids. It may also be configured so that the amount and/or concentration of the antimicrobial compound released is above a predetermined threshold for effective antimicrobial effect, either locally, or within a region exposed to the composition. Further, the solid-phase antimicrobial composition is more stable than compositions containing the individual compounds reacted to form the solid phase antimicrobial composition.

Also, the solid-phase antimicrobial composition is useful for preventing or diminishing the risk of infection even for subjects who have become resistant to antibiotics. The composition contains a solid-phase peroxyxcarboxylic acid metal salt. The peroxyxcarboxylic acid in the antimicrobial composition is able to breach the cell walls of microbes and destroy the contents of the cell, rendering the microbes incapable of developing resistance to the composition. The solid-phase form of the composition makes it easier to get the antimicrobial composition directly to or near the site of microbes, where it can destroy them.

In order for the antimicrobial composition to reach the tissue it is designed to treat or pre-treat, the article is configured in such a way as to enable contact of the article on or near the targeted tissue. It will be understood by one of ordinary skill in the art that the configuration may vary, depending on the context in which protection from microbes, or reduction or prevention of the risk of infection is sought. For example, in one embodiment of the invention, the article may be useful for treating a target such as, for example, a burn (such as for example, thermal burns, sunburns, or chemical burns), wound or cut (such as, for example, an abrasion, incision, laceration, puncture, avulsion, or amputation, whether medical, surgical, accidental or military in nature, or laser treatment wounds), dermal lesions (such as, for example, pressure ulcers, stasis ulcers, diabetic ulcers, decubitus ulcers, foot ulcers or venous ulcers). Suitable articles for this embodiment may be those that lay on or near the area to be treated, to enable the antimicrobial composition to interact with the target tissue. Suitable articles for this embodiment may include, for example wipes, bandages, cloths, surgical coverings, surgical dressings, gauze, or surgical sponges, and the like. The article may be placed directly on the target, and in some embodiments of the invention it may be held there, for example by a medical adhesive. When warranted, the article may be used in combination with negative pressure wound therapy. For example, the antimicrobial composition may be applied on and/or in a sealed wound dressing connected to a vacuum pump, in order to promote healing of acute or chronic wounds, or to enhance the healing of burns. Alternatively, the article may be placed near the target site, close enough that when contacted with body fluid or tissue, the antimicrobial composition can reach the target location in a sufficient quantity to prevent or fight infection. The article may be placed within the body cavity, for example, during surgery, to soak up fluids within the cavity, while at the same time releasing the antimicrobial composition to prevent or fight infection. Or, the article may be swiped across the target location, releasing the antimicrobial composition upon contact with body fluid or tissue at the target.

In another embodiment of the invention, the article may be useful for isolating the patient from microbes from operating personnel and/or the general environment of the operating room. Suitable articles for this embodiment may include, for example, surgical drapes. The surgical drapes may be made, for example, of woven textile fabric or nonwoven fabric. These surgical drapes may prevent runoff of fluids, that may contain bacteria from the area surrounding the operative site, into the operative wound site. Where drapes are not absorbent enough to contain all or most of the liquid, the antimicrobial composition on or in the drapes may kill bacteria in any excess fluid that may flow into the wound site, preventing or at least diminishing post-operative infection problems for the surgical patient.

In one embodiment of the invention the article of the invention may be an implant. A variety of different types of articles may be implanted in patients. One of the major problems encountered when utilizing implants is that the subject in which they are implanted may develop an infection at the site of the implant. In one embodiment of the invention, the implant is designed to replace a subject's natural bone. Such implants include, for example, artificial joints, including for example articular endoprostheses such as, for example, hip or knee implants, or dental implants, including, for example, endosteal and subperiosteal implants. In one embodiment of the invention, the antimicrobial composition may be incorporated with a bone filler and/or cement. In another embodiment, the composition may be applied on and/or in the implant in an amount that is sufficient to deter bacterial adhesion, thus minimizing prosthetic infection. In one embodiment of the invention, the applied antimicrobial composition may have a thickness of at least 10 μm.

The implant may be made of any material suitable for use for medical implants, for example, in one embodiment of the invention, the implant may be made of titanium, titanium alloy, ceramic, a polymer, stainless steel, tantalum, gold alloy, cobalt-chromium alloy, nickel-chromium alloy, and the like. In another embodiment, the implant may be applied directly on its outer surface. In a different embodiment, the antimicrobial composition may be placed on top of a coating (for example a primer coating), which may be applied to prepare the substrate for the antimicrobial coating. Examples of primer coatings include adhesion coatings. Suitable primer coatings may include, for example titanium and/or tantalum undercoatings.

In one embodiment of the invention, the implant may be configured to be temporarily inserted in the body (e.g. surgical tools). In another embodiment of the invention, the implant may be configured to be permanently or semipermanently inserted in the subject's body, such as for example, a pacemaker, defibrillator, neurostimulator, ophthalmic implant, implantable shunt, artificial joint, hip implant, knee implant, stent, implantable coil, pump, intrauterine device (IUD), heart valve, surgical fastener, surgical staple, surgical pin, surgical rod, surgical screw, implantable electrical lead, or implantable plate. In a different embodiment of the invention, the implant may be an insert inside the lumen of a medical device, such as a cannula or cannulated screw.

Any time a foreign object is implanted in a human body, there exists the possibility of infection from a variety of organisms, such as for example *Staphylococcus aureus, Staphylococcus epidermidis, Streptococcus hemolyticus*, gram-negative bacteria, *Candida albicans, Corynebacterium*, and the like. The antimicrobial composition on the articles of the invention offers the advantage of reducing or eliminating the risk of infection in patients in whom the devices have been implanted. In one embodiment of the invention, the implant may be an article that bears the antimicrobial composition directly on its outer surface. In a different embodiment, the implant may be an article that is inserted or enclosed, partially or fully, in a bioabsorbable material, that has the antimicrobial composition applied on it and/or impregnated in it. Suitable bioabsorbable materials include, for example, strands, such as for example, one or more filaments, strings or wires, that have be formed, for example, into an envelope, pouch, pocket, bag, net, mesh, or the like, woven or otherwise, and that have been configured to at least partially hold or enclose the medical device. Preferably, the bioabsorbable material has a flexible structure. The flexible structure may be configured, for example, to at least partially house a pacemaker, defibrillator, neurostimulator, ophthalmic implant, and the like. The implant may be co-implanted with the bioabsorbable material, for example, by placing the implant in the bioabsorbable material before, during or after insertion into the body. Both the implant and the bioabsorbable material may have the antimicrobial composition applied on them and/or impregnated in them, or alternatively, a device having no antimicrobial composition may be co-implanted with a biodegradable material having the antimicrobial composition applied on it and/or impregnated in it. The bioabsorbable material may be designed to degrade within the body to form a degradation product containing the antimicrobial composition, that upon contact with body fluid or tissue, diffuses into the subject's body to form an antimicrobial zone. The bioabsorbable material may be absorbed over a predetermined time period after insertion into a body. For example, the bioabsorbable material may be absorbed over hours, days, weeks, months, or years. In a preferred embodiment, the antimicrobial zone may be sustained for at least seven days.

In a different embodiment of the invention, the implant having upon or impregnated within it the antimicrobial composition may itself be bioabsorbable. The implant in this embodiment is configured to degrade within the body over time. The bioabsorbable implant may be useful, for example, for closing or treating wounds (for example sutures, staples and adhesive), repairing tissue (for example meshes, such as for hernia repair), engineering tissue (for example engineered blood vessels, skin, bone, cartilage, liver, etc.), controlling drug delivery systems (for example microcapsules and ion-exchange resins), or for prosthetic devices (for example internal bone fixation devices). The use of bioabsorbable materials in medical applications such as these may reduce tissue or cellular irritation, and the induction of an inflammatory response. The bioabsorbable implant may have any appropriate shape or structure. For example, it may be a coated strand, such as for example a filament, string or wire that is completely or partially coated with the antimicrobial composition. These coated strands may be used by themselves, for example as sutures, ties, and the like, within a subject, or they may be used to form 2D or 3D implants, for example, by weaving them.

In general, bioabsorbable materials suitable for medical applications are well known. Bioabsorbable polymers may be made from a variety of bioabsorbable resins; for example, U.S. Pat. No. 5,423,859 to Koyfman et al., incorporated herein by reference, lists exemplary bioabsorbable or biodegradable resins from which bioabsorbable materials for medical uses may be made. Bioabsorbable materials extend to synthetic bioabsorbable or naturally derived polymers. Examples of bioabsorbable polymers include, for example, polylactic acid (PLA), poly(lactic-co-glycolic acid) (PLGA), polyglycolide (PGA), polyglycoside-co-trimethylene carbonate (PGTMC), poly(caprolactone-co-glycoside), poly(dioxanone) (PDS), and poly(caprolactone) (PCL), and the like, and combinations thereof. Bioabsorbable materials may be polyester or polyactone polymers such as, for example, polymers of polyglycolic acid, glycolide, lactic acid, lactide, dioxanone, trimethylene carbonate, polyanhydrides, polyesteramides, polyortheoesters, polyphosphazenes, and copolymers of these and related polymers or monomers. Other bioabsorbable materials may be formed by proteins (such as, for example, albumin, fibrin, collagen, or elastin), as well as polysaccharides (such as, for example, chitosan, alginates, or hyaluronic acid), or biosynthetic polymers (such as, for example, 3-hydroxybutyrate polymers).

Biological weapons contain a number of disease-producing agents, such as bacteria, viruses, rickettsiae, fungi, toxins, or other biological agents, that may be utilized as weapons against humans, animals, or plants. Dermal or inhalation exposure to such chemical nerve agents presents threats such as muscle paralysis, shortness of breath, seizures, or even death. The same properties that make the antimicrobial composition useful to treat or prevent infection also make it useful for treating persons and other subjects exposed to chemical nerve agents. Thus, in one embodiment of the invention, the articles and methods of the invention enable the pre- or post-treatment of both the broken or unbroken skin of subjects who may be exposed to such agents. Likewise, the articles and methods of the invention also make the invention suitable for use in fungal treatment. Therefore, in another embodiment of the invention, the articles and methods of the invention enable the treatment and prevention of fungal infections, for example foot or nail fungal infections.

The antimicrobial composition on the medical device contains a solid-phase peroxyxcarboxylic acid metal salt. The solid-phase peroxyxcarboxylic acid metal salt may be made by mixing hydrogen peroxide, a peroxycarboxylic acid, a basic metal salt, to form a solid-phase peroxycarboxylic acid metal salt precipitate. The reaction to form the solid-phase peroxyxcarboxylic acid metal salt may be performed in a solvent, which may be water, or a lower (water-soluble) alcohol, such as, for example, methanol, ethanol, isopropanol and the like. If the peroxycarboxylic acid is not partially, or completely, miscible in the aqueous reaction solution or suspension, the peroxycarboxylic acid may first be solubilized, for example by pre-dissolving it in an organic solvent. Suitable organic co-solvents include, for example, ethyl acetate, t-butyl alcohol, methanol, tetrahydrofuran, tetrahydropyran, and ethanol and mixtures thereof, with ethyl acetate and t-butyl alcohol being most preferred. Some organic solvents are not preferred because they can react with the peroxycarboxylic acids. This group includes dimethyl sulfoxide, carbon disulfide, and solvents which contain multiple bonds. Also, it is desirable that the organic co-solvent selected not solubilize the metal peroxycarboxylate product to a significant extent. This will facilitate the isolation of the product as a solid precipitate. The precipitate may be separated by any standard technique. For example, filtration, decantation, and/or centrifugation can be used. The precipitate may then be washed, for example, with water, and if used, an organic co-solvent, to remove any unreacted starting materials. Finally, the precipitate is dried to remove excess water. This may be achieved by any standard means of drying. For example, vacuum desiccation, mild heating at ambient pressure, or air drying may be used.

In one embodiment of the invention, the amount of basic metal salt added to the reaction mixture is sufficient to adjust the pH of the reaction solution to, from about 2 to about 8, preferably from about 3.5 to about 7.5, more preferably from about 3.8 to about 7, and most preferably less than 5. Lower pHs are preferred as the peroxycarboxylic acid may rapidly destruct at high pH, which undesirably reduces the amount of retained peroxycarboxylic acid. In a preferred embodiment, the pH of the reaction solution is lower than the $pK_a$ of the peroxycarboxylic acid. For example, in one embodiment, the reaction may take place at a pH of from about 3.8 to about 7.5, when using peroxyacetic acid, which has a $pK_a$ of 8.2. The molar ratio of peroxycarboxylic acid to basic metal salt may vary, depending on which basic metal salt is being used. The preferred ratio is that which enables essentially all of the metal and peroxycarboxylic acid to interact, and essentially none of each compound to be wasted. In another embodiment of the invention, the amount of metal from the metal salt, and the amount of peroxycarboxylic acid utilized in the reaction solution or suspension, is such that the molar ratio of metal to peroxycarboxylic acid is from about 0.1:1 to about 10:1. In a different embodiment of the invention, the molar ratio of metal to peroxycarboxylic acid is from about 0.5:1 to about 8:1. In another embodiment of the invention the molar ratio of basic metal salt to peroxycarboxylic acid is about 6:1. In yet another embodiment of the invention the molar ratio of metal to peroxycarboxylic acid is about 1.5:1. In still another embodiment of the invention, the molar ratio of metal to peroxycarboxylic acid is about 0.7:1. In a further embodiment of the invention, the antimicrobial composition contains from about 0.1 wt % to about 85 wt % of the peroxycarboxylic acid.

The peroxycarboxylic acid includes a compound having the formula R(C000H)n, in which R can be hydrogen, alkyl, alkenyl, alicyclic group, aryl, heteroaryl, or heterocyclic group, and n is 1, 2, 3, or greater than 3. R may include functional groups such as, for example, carboxylic acid, alkyl, ether, amide or amine functional groups. Preferably R includes alkyl or carboxylic acid groups. The term "alkyl" includes a straight or branched saturated aliphatic hydrocarbon chain having from 1 to 12 carbon atoms, such as, for example, methyl, ethyl, propyl, isopropyl (1-methylethyl), butyl, tert-butyl (1,1-dimethylethyl), and the like. The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. Any peroxycarboxylic acid may be used in the antimicrobial composition. Examples of suitable peroxycarboxylic acids range from those with relatively high stability in solution, such as for example peracetic acid, perpropionic acid, perbutyric acid, perisobutyric acid, permalonic acid, persuccinic acid, perglutaric, permaleic, percitraconic, perbenzoic, or perphthalic acid, and those with shorter solution-phase lifetimes, for example performic acid, perlactic acid, or perglycolic acid. In one embodiment of the invention, the peroxycarboxylic acid is non-cationic. In this embodiment the reaction mixture has a pH such that the peroxycarboxylic group is protonated. Examples of suitable non-cationic peroxycarboxylic acids include any peroxycarboxylic acid without other ionizable groups on the molecule. Acceptable groups include, for example, alkyls, aryls, alkenyls, alkynyls, ethers, esters, amides, alcohols, and ketones in both branched and unbranched structures. Specific examples of non-cationic peroxycarboxylic acids include peroxyformic, peroxyacetic, peroxypropionic, peroxybutyric, peroxyisobutyric, peroxyvaleric, peoxyisovaleric, peroxypivalic, methoxyperoxyacetic, peroxyglycolic, peroxylactic, peroxybenzoic, peroxycrotonic, and perpropiolic acid. In a different embodiment of the invention, the peroxycarboxylic acid is cationic. In this embodiment, the reaction mixture also includes a counteranion. Suitable cationic peroxycarboxylic acids include, for example, those having cationic moieties containing nitrogen atoms, such as quartenary ammonium or substituted pyridines. Suitable counteranions include any negatively charged species that is chemically compatible with the oxidative composition over the time scales of interest. These include, for example, chloride, phosphate, hydrogen phosphate, dihydrogen phosphate, sulfate, hydrogen sulfate, nitrate, perchlorate, organic carboxylates, carbonate, hydrogen carbonate, fluoride, selenite, and the like.

The basic metal salts serve to stabilize the antimicrobial composition. It is well known in the art that peroxycarboxylic acids are highly volatile due to their high vapor pressures. They are also known to readily lose their active oxygen, making them unstable. By "active oxygen" is meant the oxygen contained in a molecule that is easily transferred via a chemical reaction to another compound. Peroxycarboxylic acids tend to be even more unstable when mixed with other compounds. As a result, compositions containing peroxycarboxylic acids have poor storage stability. Previous attempts to provide medical devices and substrates coated with an antimicrobial solution of the hydrogen peroxide and peroxycarboxylic acid were unsuccessful in the absence of the basic metal salt, due in large part, to loss, during the drying process, of most of the peroxycarboxylic acid from the formulation, due to volatilization. In addition, the liquid antimicrobial composition suffered comparable losses of hydrogen peroxide, resulting in a final antimicrobial composition that did not have the desired antimicrobial properties. The formation of the solid-phase peroxycarboxylate metal salt overcomes the challenge of maintaining the volatile components of the antimicrobial composition, producing a dry antimicrobial composition having the desired properties. The addition of basic metal salts to the antimicrobial composition is thus useful for achieving a quantifiable amount of peroxycarboxylic acid in the antimicrobial composition, even though the more volatile species are still lost. The peroxycarboxylate moiety of the antimicrobial composition's peroxycarboxylic acid associates with the metal in the basic metal salt in such a way that provides stability to the solid-phase peroxycarboxylic acid metal salt. In other words, the active oxygen in the metal peroxycarboxylate is retained during storage to a greater extent than is the active oxygen contained in the corresponding peroxycarboxylic acid. Also, the solid-phase peroxycarboxylic acid metal salts have superior odor, dispersibility and handling properties relative to the corresponding peroxycarboxylic acids. The long-term stability of the solid-phase peroxycarboxylic acid metal salt may be negatively affected by the presence of water. Therefore, during drying of the solid-phase peroxycarboxylic acid metal salt precipitate, it is desirable to eliminate as much of the solution-phase water as possible. In a preferred embodiment, only waters of crystallization are present in the solid-phase peroxycarboxylic acid metal salt. In another preferred embodiment, the solid-phase peroxycarboxylic acid metal salt contains no more than 12 water molecules per metal ion, with the amount of acceptable water molecules depending on the peroxycarboxylic acid being used. Suitable metals for the basic metal salts include, for example magnesium, zinc and lithium, with magnesium and zinc being preferred, and magnesium salts being highly preferred. The basic metal salt may be, for example, hydroxide, carbonate, acetate, oxide, or formate salts. The basic metal salt may also be the metal salt of the organic acid corresponding to the reduced form of the peroxycarboxylic acid (i.e. an organic anion that is the reduced form of its peroxycarboxylic acid), for example magnesium formate may be used when forming magnesium peroxyformate, and lithium acetate may be used when forming lithium peracetate.

The stability of the antimicrobial compositions on or in the articles of the invention may also be affected by the humidity under which the articles are stored. In one embodiment of the invention, the articles are stored under conditions where the relative humidity is less than about 43, preferably less than about 40, more preferably less than about 35.

In another embodiment of the invention, the reaction solution or suspension may also contain other additives. For example, in one embodiment of the invention, the reaction solution or suspension may also include a polyethylene glycol (PEG). Any type of polyethylene glycol may be used for the invention, whether a low molecular weight PEG, such as for example, PEG 200, PEG 300 or PEG 400, a high molecular weight PEG, such as for example PEG 3350, PEG 4000, PEG 10,000 or PEG 35,000, or a medium molecular weight PEG. The amount of polyethylene glycol will depend on a variety of factors, such as for example, the application or the type of peroxycarboxylic acid. In one embodiment of the invention, the polyethylene glycol is present in the reaction mixture in an amount of from greater than 0 to 75 weight percent, based on the total weight of the reaction mixture.

Although particular attention and examples of types of articles and surfaces have been described, it should be readily understood that any substrate surface that will come into contact with bodily fluids may benefit from an antimicrobial effect, including articles that are not inserted or implanted into a body.

The present invention is also directed toward methods of reducing the risk of infection in a subject. In one embodiment of the invention, the subject may be the recipient of a surgical implant, including for example, those described herein-above. Another embodiment is directed toward a method reducing the risk of infection in a subject by applying to a surface the solid-phase antimicrobial composition containing the solid-phase peroxycarboxylic metal salt which is the reaction product of a solution or suspension containing hydrogen peroxide, a peroxycarboxylic acid, and a basic metal salt. Preferred basic metal salts are as described herein-above. The surface on which the antimicrobial composition is applied may be an article configured for tissue contact, as described herein-above, or a body tissue, also as described herein-above.

Another embodiment of the invention is a method of reducing the risk of infection in subjects by forming the solid-phase peroxycarboxylic acid metal salt antimicrobial composition in the manner described herein-above, and then applying the composition to either the surface of an article configured for tissue contact, as described herein-above, or the surface of a body tissue, also as described herein-above.

EXAMPLES

Example 1. Addition of Basic Salts

In a previous comparative experiment, plastic substrates coated with a liquid antimicrobial composition were found to lose effectively all of their peracetic and acetic acids, and the vast majority of their hydrogen peroxide, within only a few weeks. Another test showed that glass coated with PEG-containing antimicrobial solution lost the vast majority of these species in only 24 hr at 40° C. (95% hydrogen peroxide, ~99.7% acetic acid, and ~99.97% peracetic acid).

This example was designed to assess peracid retention in dry antimicrobial compositions containing a basic salt, by performing tests on both relatively inert substrates (glass and plastic), as well as titianium-coated PEEK substrates, which were the implant substrates.

A dry antimicrobial composition was prepared by mixing a antimicrobial solution with basic metal salts. The antimicrobial solution contained hydrogen proxide, acetic acid, peracetic acid and water. The boiling points of these materials are as follows: water=100° C., hydrogen peroxide=150° C., acetic acid=118° C., and peracetic acid=105° C. Their vapor pressures at 25° C. are: water=3200 Pa, hydrogen peroxide=260 Pa, acetic acid=2050 Pa, and peracetic acid=2100 Pa.

A base was added to the antimicrobial solution. The amount of base required to reach the desired pH was calculated using p=1.10 g/mL. The antimicrobial solution contained:

Hydrogen peroxide=7.00 M
Acetic acid=2.75 M
Peracetic acid=1.70 M

All other impurities were considered negligible for pH calculations. Considering that >3 M base would be required to raise the pH to just 5.0, the antimicrobial solution was freshly diluted, and mixed with PEG, and a base. Although the dilution may seem counterintuitive, the concentration reduction would only have a small effect compared to the significant benefits of deprotonation. As an example, if 10% antimicrobial solution were used instead of 80%, the overall concentration would drop to 12.5% of what it was. But if the pH were simultaneously increased from about 2.0 to 6.5, the fraction of peracetic acid that would be deprotonated would increase from $5.0 \times 10^{-7}$ to 0.016. Including the reduction induced from dilution, this would be a net improvement of 3900×.

To balance the added basic salt content with the dilution, the fraction of antimicrobial solution used in antimicrobial composition formulations in this study was 20%. The amount of PEG 3350 was 20% by mass. The remainder was water and a basic salt to achieve the desired pH. The pH's tested in this work were unmodified, pH 5, and pH 7.5. It was realized that the calculated pH values could differ from actual ones (and that the solution pH's would likely change over time), so when a solution was identified by pH, the calculated pH was used as the descriptor.

A quick test study was done at 12.5% antimicrobial solution and 20% PEG, and the nonvolatile components were readily retained, while the volatiles were lost. Additionally, non-volatiles were also retained in 80% antimicrobial solution/20% PEG prepared in a commercial coater. Thus, the chosen dilution would be between these other two formulae. At 20% antimicrobial solution, the concentrations of the antimicrobial solution components would be ⅕ of the values listed above, therefore dominated by 550 mM acetic acid. The calculated native pH of this dilution was 2.41. Multiple salts were considered for achieving the desired pH. Acceptable salt anions were acetate (already present in formulation), phosphate (already present in vivo), and those that were consumed by the buffer (hydroxide and carbonate). The concentrations needed to achieve the desired pH were listed in Table 1.1.

TABLE 1.1

Salts and their Concentrations to Reach pH 5 in the Antimicrobial Solution.

| Salt | Conc (mM) | Cation Conc (mM) |
| --- | --- | --- |
| Sodium phosphate (tribasic) | 198 | 594 |
| Sodium hydroxide | 395 | 395 |
| Potassium phosphate (tribasic) | 198 | 594 |
| Potassium hydroxide | 395 | 395 |
| Magnesium phosphate hydrate | 97 | 294 |
| Magnesium hydroxide | 197 | 197 |
| Calcium hydroxide | 197 | 197 |

It was unknown if magnesium phosphate has high enough solubility to achieve the above concentration.

For pH 7.5, the only salts that could reach the desired pH at reasonable concentrations and a 20% antimicrobial solution fraction were the hydroxide salts. The necessary concentrations were listed in Table 1.2.

TABLE 1.2

Salts and their Concentrations to Reach pH 7.5 in the Antimicrobial Solution

| Salt | Conc (mM) | Cation Conc (mM) |
| --- | --- | --- |
| Sodium hydroxide | 619 | 619 |
| Potassium hydroxide | 619 | 619 |
| Magnesium hydroxide | 309 | 309 |
| Calcium hydroxide | 309 | 309 |

The base concentrations selected were above the unoxidized organic acid concentration in the diluted antimicrobial solution (~560 mM).

The antimicrobial solutions were prepared in cleaned HDPE vials. 15 mL of antimicrobial solution was prepared with an assumed density of p 1.05 g/mL, equating to 15.75 g. Materials were added in the following order: PEG, salt, water, antimicrobial solution (unless a salt solution was employed, in which case the order was PEG, water, salt solution, antimicrobial solution). 3.15 g (20 wt %) was PEG 3350. The antimicrobial solution had p 1.10 g/mL. To obtain ~20% molar concentration antimicrobial solution, required 3.0 mL of antimicrobial solution (3.3 g). The necessary salt mass was calculated from the concentrations in Tables 1.1 & 1.2, the molecular weight, and the 15 mL volume. This was done with the formula:

Mass (mg)=Concentration (mM)×1/MW (mg/mmol)× 0.015 L

The mass was either added directly, or as a concentrated solution (e.g. 2 M). The remaining water necessary was added as: 15.75 g minus (3.15 g PEG+3.30 g antimicrobial solution+X g salt or salt solution). After all of the components were added, the solution was mixed, and used for antimicrobial composition application immediately (within 1 hr). PH measurements were taken, using a separate aliquot, so as not to contaminate the antimicrobial composition.

The antimicrobial composition was applied in two ways. It was applied on a glass substrate by simple addition of a small amount of antimicrobial composition, and permitting evaporation. Here, the glass substrate was a glass HPLC vial. The second way it was applied was using a spin coater to apply a thin layer of the antimicrobial composition, which was used on Ti-plated PEEK square coupons and on other substrates that were more likely to have an "inert" surface.

The "glass vial" experiments were performed by cleaning glass HPLC vials with pure water and then drying. Vial mass was measured to the nearest 0.01 mg. 20 μL of antimicrobial composition was added to the bottom of the vial, and the mass of this addition was be measured to the nearest 0.01 mg. No rotating of the vial was performed to try to achieve uniform application on all sides, as preliminary attempts to do this found it to be difficult and time consuming. Instead, a thicker but more reproducible application was achieved with this approach. The vial was placed upright in storage and the start time recorded. Vial masses were recorded multiple times throughout the drying process. The minimum number of time points were one at 2 hr and at least once per day after that, until a steady-state mass was reached. When taking the mass, the vial was allowed to cool for 5 min before the measurement, to improve measurement precision. Time of measurement was recorded.

Direct-injection analysis was performed on the antimicrobial composition by extracting the antimicrobial composition into 180 μL of a pH 2.1 phosphate eluent using gentle hand swirling/mixing. Extraction time was the longer of 3 min, or time until all visible antimicrobial composition was dissolved, plus 1 min. The extract was then immediately transferred to a small-volume HPLC insert and analyzed by direct-injection HPLC analysis. Four vials of each antimicrobial composition condition were prepared and monitored over time, with the first direct injection taking place at 2 hr of age and then roughly once per day after that. Direct injections were not done on all four vials if earlier vials in the experiment showed no successful retention.

Several points above warrant discussion. First, 20 μL of antimicrobial composition would yield an antimicrobial composition of ~42 μm in thickness if only PEG remained after drying, assuming a vial inner diameter of ~1.03 cm, and uniform application. While thicker than the anticipated final applied antimicrobial composition thickness of 10 μm, the thickness is still of the same order of magnitude. Second, if PEG was the only significant species remaining in the antimicrobial composition, the dilution would be 2.3% g antimicrobial solution/mL for the analysis. Dilution was performed in pH 2.1 phosphate instead of water in order to help mitigate matrix effects from the elevated pH of the samples. Specifically, the molarity of base at pH 7.5 was ~620 mM, which equated to 69 mM for 20 μL dried and reconstituted into 180 μL (note that acetate would be 61 mM in this case). The pH 2.1 phosphate eluent was a specialty solution composed of 50 mM KH2PO4 and 66 mM H3PO4 (6.8045 g/L KH2PO4 and 4.505 mL 85% H3PO4/L) that is designed to mitigate this. Specifically, this eluent with the above amounts of base and acetate present would yield an extract of pH ~3.7, where >90% of the acetate was protonated. In contrast, if the stock HPLC eluent was used, the final pH would be ~5.4. For the pH 5 study (44 mM Na after elution), the calculated extract with the specialty eluent was pH ~2.7.

Vials were stored under two different sets of conditions. The first set was kept at 40° C. in an oven, whereas a second was maintained at room temperature (~21° C.). The 2 hr time mentioned earlier was for the 40° C. experiment, while the room-temperature ones could be measured at a later time given their slower evaporation. Overall, 96 individual vials were monitored: 2 temperatures×4 vials/condition×(1 unmodified pH+7 pH 5 solutions+4 pH 7.5 solution).

The Ti-plated PEEK coupons (½"×½") were coated by pipetting an aliquot on the surface, and allowed to dry in a 40° C. oven. Again, both 40° C. and room-temperature (~21° C.) tests were performed.

Example 1 Results

Testing of the addition of basic salts to PEG-containing antimicrobial solution showed no peracid retention for sodium, potassium, or calcium. However, the addition of magnesium hydroxide was observed to improve peracid retention (as peracetic acid or its salt) in the antimicrobial composition. Peracetate retention in a magnesium-enhanced antimicrobial composition was measured at 0.9% after six days at 40° C., whereas the other salts showed complete loss at that time. Even after 15 days, the 40° C. sample retained 0.8% of the original peracetic acid. Smaller amounts of peracetic acid were still measurable on these time scales for antimicrobial compositions with a lower concentration of magnesium. For comparison, a six-month shelf life at 23° C. could be claimed with an accelerated-aging test of ~57 days at 40° C., so this test was roughly 26% of the required time.

The study found that all of the basic salts showed relatively rapid peracid decomposition, when attempting to prepare a pH 7.5 antimicrobial solution, as evidenced by gas evolution and a decreasing pH over time. This phenomenon was also exhibited by both the magnesium and calcium salts at lower concentrations, targeting pH 5.0. Thus, these alkaline earth metal salts were only tested in the heated study (40° C.) and not the room-temperature study. Results showed that all measurable peracetic acid was gone within days for all of the salts tested at room temperature. Results were similar at 40° C., but with one important exception—the magnesium salts (two concentrations of magnesium hydroxide) retained measurable peracetic acid. Calculated peracetic acid retentions for these experiments are shown in Table 1.3. It is unknown why the first time point at the higher magnesium concentration gave the lowest yield. Of particular note is that at pH 5 only ~0.05% of the peracetic acid was expected to be deprotonated, yet the measured retention at 15 days was 0.26%, or 5×higher. The pH may have been lower than 5.0 due to peracetic decomposition—after 6.5 hr the antimicrobial solution's pH was measured at 4.50, whereas sodium and potassium salts made in similar ways were 4.94 and 4.86, respectively. This indicates that peracetic acid may not have to be deprotonated to complex with magnesium.

TABLE 1.3

Measured peracetic acid retention for two Mg(OH)$_2$-PEG-antimicrobial solution compositions containing 20 wt % PEG and 21 wt % antimicrobial solution at 40° C.

| EXAMPLE 1.0 | | EXAMPLE 1.1 | |
|---|---|---|---|
| 197 mM Mg(OH)$_2$ | | 309 mM Mg(OH)$_2$ | |
| (Expect pH 5.0) | | (Expect pH 7.5) | |
| Age | Peracetic Retention | Age | Peracetic Retention |
| 2.5 hr | 1.1% | 2.9 hr | 0.24% |
| 1.1 day | 1.0% | 1.0 day | 1.2% |
| 3.0 day | 0.34% | 6.1 day | 0.89% |
| 15.3 day | 0.26% | 14.9 day | 0.80% |

Note that the targeted pH 7.5 solution was observed to have considerable gas evolution, and the pH was measured at 4.88 after 4.5 hr. While the pH calculations were not expected to be perfect, their precision should have been far superior than such a large discrepancy would imply, indicating decomposition to the more acidic parent acid.

TABLE 1.4

Measured peracetic acid retention for PEG- antimicrobial solution compositions containing 20 wt % PEG and 21 wt % antimicrobial solutions containing other added salts when dried at 40° C. BDL = below detection limit. Only "likely dry" time points are included for brevity.

| | Salt Added (Concentration) | Time Point 1 (Age) | Time Point 2 (Age) | Time Point 3 (Age) |
|---|---|---|---|---|
| | None | 0.05% (1.1 days) | BDL (2.2 days) | BDL (15.2 days) |
| EXAMPLE. 1.3 | Mg(OH)$_2$ (1.1 wt %) | 1.12% (1.1 days) | 0.33% (3.0 days) | 0.23% (15.3 days) |
| EXAMPLE. 1.4 | Mg (OH)$_2$ (1.7 wt %) | 1.29% (1.0 days) | 0.99% (6.1 days) | 1.01% (14.9 days) |
| COMPARATIVE EXAMPLE 1.5 | Ca(OH)$_2$ (1.4 wt %) | BDL (1.1 days) | BDL (3.1 days) | BDL (15.8 days) |
| COMPARATIVE EXAMPLE 1.6 | Ca(OH)$_2$ (2.2 wt %) | BDL (1.0 days) | BDL (6.1 days) | BDL (14.9 days) |
| COMPARATIVE EXAMPLE 1.7 | NaOH (1.5 wt %) | BDL (1.0 days) | BDL (6.8 days) | BDL (15.0 days) |
| COMPARATIVE EXAMPLE 1.8 | NaOH (2.4 wt %) | BDL (1.8 days) | BDL (6.9 days) | BDL (15.0 days) |
| COMPARATIVE EXAMPLE 1.9 | KOH (2.1 wt %) | BDL (1.1 days) | BDL (3.0 days) | BDL (15.8 days) |

TABLE 1.4-continued

Measured peracetic acid retention for PEG- antimicrobial solution compositions containing 20 wt % PEG and 21 wt % antimicrobial solutions containing other added salts when dried at 40° C. BDL = below detection limit. Only "likely dry" time points are included for brevity.

|  | Salt Added (Concentration) | Time Point 1 (Age) | Time Point 2 (Age) | Time Point 3 (Age) |
|---|---|---|---|---|
| COMPARATIVE EXAMPLE 1.10 | KOH (3.3 wt %) | BDL (1.8 days) | BDL (6.9 days) | BDL (15.0 days) |
| COMPARATIVE EXAMPLE 1.11 | $Na_3PO_4 \cdot 12H_2O$ (7.1 wt %) | 0.28% (1.1 days) | BDL (3.0 days) | BDL (15.2 days) |
| COMPARATIVE EXAMPLE 1.12 | $K_3PO_4$ (3.9 wt %) | BDL (1.1 days) | BDL (3.0 days) | BDL (15.2 days) |

Example 2. Magnesium Salt Identity and Concentration Studies, and Alternative Salt Studies This example was designed to evaluate the performance of antimicrobial solutions containing magnesium-based additives. Vaporization and chemical-induced loss processes were assessed by performing tests on relatively inert substrates (glass). This work was intended to provide information on antimicrobial composition stability. The magnesium salt studies were performed in a similar way as the studies in Example 1, but with a range of concentrations to see if the retention could be improved.

Despite the changing pH over time, experiments were designed for a target pH. For this work, the amount of base required to reach a desired pH was calculated using ρ=1.126 g/mL, and the same composition of antimicrobial solution as that used in Example 1, was utilized here. All other impurities were considered negligible for pH calculations. Because >3 M base would be required to raise the pH to just 5.0, antimicrobial compositions included freshly diluted antimicrobial solutions, PEG, and a base, just as in Example 1.

Magnesium salts studied included hydroxide, acetate, carbonate, chloride, and nitrate salts. The hydroxide and carbonate salts were already shown to be inferior to the acetate at 197 mM for both temperatures in Example 1. Thus, they were only tested at the lower concentration to establish if they would deviate from the acetate at the lower pH. Magnesium chloride was tested for the first time, and only the lowest concentration was employed in order to minimize catalytic destruction of the peracid by chloride, and also to be able to directly compare with the other salts. The nitrate salt was also added, because it was a way to introduce magnesium without raising the pH or adding an anion that would catalytically destroy active oxygen. The acetate salt was tested at four concentrations bracketing the 197 mM value tested in Example 1. Employed PEG concentrations were 20 wt %, to permit direct comparison with the work in Example 1. Note: for all PEG solution densities listed in the rest of the document, the density was estimated using data from Mei, et al., *J. Chem. Eng. Data* (1995), 40, 1168-1171.

9 ml of antimicrobial compositions having an assumed density of ρ≈1.037 g/mL, equating to 9.335 g, were prepared in clean and dry HDPE vials. Materials were added in the following order: PEG solution, salt, water, and antimicrobial solution. All additions were measured by mass. PEG was 5.334 g (5.14 mL for ρ≈1.037 g/mL) of a 35 wt % PEG 3350 solution. This solution was prepared using equal masses of PEG and water in a clean vial. The necessary salt mass was calculated from the concentrations in Table 2.1, the molecular weight, and the 9 mL volume. This was done with the following formula, and the resultant masses are also given in Table 2.1:

Mass (mg)=Concentration (mM)/MW (mg/mmol)×0.009 L

The remaining water necessary was added as: 9.335 g minus (5.334 g PEG solution+1.867 g antimicrobial solution+X g salt or salt solution); see Table 2.1 for masses. The antimicrobial solution had ρ≈1.126 g/mL. To obtain ~20 wt % antimicrobial solution required 1.66 mL antimicrobial solution (1.867 g). For any trials with $MgCO_3$, mass was not measured in this step. After all of the components were added, the solution was mixed, and then used for antimicrobial composition aliquots immediately upon full dissolution. Solution vials were appropriately vented to permit gas escape. pH measurements of the antimicrobial solution were taken several times, after the antimicrobial composition aliquots were added to vials, in order to monitor any changes in pH with time. No pH measurements were made before antimicrobial composition application, to avoid KCl contamination in the antimicrobial composition from electrode leaching.

TABLE 2.1

Magnesium-based Additives, Target Solution pH, Desired Concentrations, and Required Masses for 9-mL Antimicrobial Solutions

|  | Metal Salt | Expected pH | Concentration (mM) | Salt Mass (mg) | Water (g) |
|---|---|---|---|---|---|
| COMPARATIVE EXAMPLE 2.1 | MgC12•6H2O | 2.42 | 85 | 155.5 | 1.978 |
| COMPARATIVE EXAMPLE 2.2 | Mg(NO3)2•6H2O | 2.42 | 85 | 196.2 | 1.938 |
| EXAMPLE 2.3 | Mg(OH)2 | 4.26 | 85 | 44.6 | 2.089 |
| EXAMPLE 2.4 | MgCO3 | 4.25 | 85 | 64.5 | 2.069 |
| EXAMPLE 2.5 | Mg(Ac)2•4H2O | 4.10 | 85 | 164.1 | 1.970 |
| EXAMPLE 2.6 | Mg(Ac)2•4H2O | 4.32 | 141 | 272.1 | 1.862 |
| EXAMPLE 2.7 | Mg(Ac)2•4H2O | 4.59 | 253 | 488.3 | 1.645 |
| EXAMPLE 2.8 | Mg(Ac)2•4H2O | 4.69 | 309 | 596.4 | 1.537 |

For the above table, each row was tested at both room temperature and 40° C. Each row-temperature combination also used six vial samples, meaning a total of 96 samples, many having multiple mass time points measured.

The antimicrobial composition was applied on a glass substrate, by addition of a small amount of antimicrobial solution, followed by evaporation. Here, the glass substrate was a glass HPLC vial. The "glass vial" experiments were performed by first cleaning glass HPLC vials with 18.2

MΩ×cm water, and drying. Vial mass was measured to the nearest 0.01 mg. 20 µL of antimicrobial solution was added to the bottom of the vial, and the mass of this addition was measured to the nearest 0.01 mg. The vial was placed upright, either at room temperature or in a 40° C. oven, and the start time was recorded (which was liquid-addition time at room temperature, or oven-placement time at 40° C.). Vial masses were recorded multiple times throughout the drying process. The minimum number of time points was one at ~1-3 hr, and at least once per day after that, until a near-steady-state mass was reached (which should take ~1 day). When taking the mass, oven vials were allowed to cool ~5 min before the measurement, to improve measurement precision. Likewise, the vial was allowed to sit on the balance for at least 60 sec to obtain best results. Time of measurement was recorded (oven-removal time for 40° C. vials).

Direct-injection analysis was be performed on the antimicrobial composition by extracting the antimicrobial composition into 180 µL of a pH 2.1 phosphate eluent (described in Example 1). The extraction date/time was recorded. Extraction time was the longer of 3 min of time, or until all visible antimicrobial composition was dissolved, plus 1 min. The extract was then immediately transferred to a small-volume HPLC insert, and analyzed by direct-injection HPLC analysis. To help avoid cumulative buildup of PEG on the HPLC column, 50/50 vol % methanol/water rinses were performed at the start and end of experimental days. Six vials of each antimicrobial composition condition were prepared and monitored over time, with the first direct injection taking place within one day of application, and the second taking place on the next business day. Direct injections were not done on all six vials if earlier vials in the experiment showed no successful retention. In contrast, if a highly successful formulation was found, the final vial had peracid-derivatization analysis done on it in addition to direct-injection analysis.

Previous studies with salt additions utilized ~20 wt % antimicrobial solution, while varying the salt identity and/or concentration. This study also evaluated the effect of dilution by changing antimicrobial solution concentration, while keeping other variables constant. PEG was kept at 20 wt %. The salt was magnesium acetate at a concentration of 197 mM. All solutions were prepared at 9 mL volumes, with an assumed $\rho \approx 1.037$ g/mL, for a total solution mass of 9.335 g. Antimicrobial solutions and application were performed as described above, but the conditions listed in Table 2.2 were used. Note that each condition included 380.2 mg of Mg(Ac)$_2$·4H$_2$O and 5.334 g (5.143 mL) of 35 wt % PEG. The expected pH was calculated assuming molar concentrations in antimicrobial solution dropped by the wt % (that is, densities were ignored), which was an approximation.

TABLE 2.2

Parameters for the Antimicrobial Solution Concentration Study for Mg(Ac)$_2$-Based Antimicrobial Compositions.

| | ANTI-MICROBIAL SOLUTION (wt %) | ANTI-MICROBIAL SOLUTION (mL) | Water (g) | Expected pH |
|---|---|---|---|---|
| EXAMPLE 2.9 | 8 | 0.633 | 2.874 | 4.88 |
| EXAMPLE 2.10 | 14 | 1.161 | 2.314 | 4.63 |
| EXAMPLE 2.11 | 26 | 2.155 | 1.193 | 4.36 |
| EXAMPLE 2.12 | 32 | 2.653 | 0.633 | 4.27 |

Note that a 20 wt % sample at these conditions was already collected in Example 1 and was also compared.

These experiments were performed the same the ones above—two temperatures and six vials each, totaling 48 vials for this experiment.

This study also evaluated the effects of PEG concentration. One experiment in Example 1 used no PEG, and results indicated that the PEG content did not significantly affect retention. To verify this, PEG concentrations of 10 wt % and 30 wt % were tested. For both PEG concentrations, 197 mM magnesium acetate (380.2 mg) and 20 wt % antimicrobial solution were used in order to directly compare against previous results with 20 wt % PEG. 9 mL of solution were prepared both times. These solutions were made similarly to those above, except that PEG solid was used, and the addition order was salt before PEG, instead of the reverse. For the 10 wt % PEG test, the anticipated density was ~1.019 g/mL, giving a total solution mass of 9.167 g. Mass of PEG solid needed was 0.9167 g. Antimicrobial solution requirement was thus 1.833 g (1.628 mL), and the required water was 6.036 g. For the 30 wt % PEG test, the anticipated density was ~1.055 g/mL, giving a total solution mass of 9.497 g. Mass of PEG solid needed was 2.849 g. Antimicrobial solution requirement was thus 1.899 g (1.687 mL), and the required water was 4.368 g. Antimicrobial composition application in the vials was done as described above. The same two-temperature and six-vial approach was also used, meaning 24 vials were used in this experiment.

This study also tested possible alternatives to magnesium salts. These tests were carried out using the same protocols as those used for Magnesium salts (20 wt % antimicrobial solution and 20 wt % PEG). Salt concentrations were chosen at the time of the experiment, based upon the most successful magnesium salt results at the time of testing.

Example 2 Results

Results from the salt screening experiment described in Table 2.1 indicated that antimicrobial compositions containing magnesium chloride and magnesium nitrate did not provide peracetic acid retention, while those containing magnesium hydroxide, magnesium carbonate and magnesium acetate did provide peracetic acid retention (with magnesium acetate providing the highest retention, followed by magnesium carbonate, and then magnesium hydroxide). Those compositions having higher concentrations of magnesium acetate yielded higher peracid retentions.

Preliminary results from the experiment described in Table 2.2 indicated that higher peracid content remained in the antimicrobial composition as the antimicrobial solution concentration increased, with antimicrobial compositions containing 32% antimicrobial solution having the highest peracid content and being the highest concentration. The antimicrobial solutions having the lowest concentration showed the higher percent peracid recovery, but had the lower overall peracid loading (lower mass to start with). Higher concentrations had higher mass loadings, and yield appeared to level out.

Experiments on improving the antimicrobial composition formulation to achieve a measurable amount of peracid by the addition of basic salts were performed. A final report from these experiments was not finalized, but it was concluded that the formulations which yielded a measurable amount of peracid are the PEG-magnesium acetate-antimicrobial solution-alcohol combination and the PEG-magnesium acetate-water-antimicrobial solution.

Example 3. Higher Antimicrobial Solution Concentrations and Antimicrobial Composition Aging Study The objective of this study was to evaluate higher concentrations of antimicrobial solution, and antimicrobial composition aging. These were prepared directly from solid PEG, antimicrobial solution liquid concentrate, and magnesium acetate. Table 3.1 provides the masses for each of these. These were prepared in the same way as the experiments in Table 2.2, except that solid PEG was used, and the total mass of the prepared antimicrobial solution was 5 g.

TABLE 3.1

Formulations for High-Concentration Antimicrobial Solution Polymer Coatings

|  | Final Antimicrobial Solution Content | Antimicrobial Solution (g) | Antimicrobial Solution (mL) | PEG (solid, g) | $Mg(Ac)_2 \cdot 4H_2O$ (mg) | $H_2O$ (g) |
|---|---|---|---|---|---|---|
| EXAMPLE 3.1 | 39.7% | 2.015 | 1.776 | 1.003 | 215.24 | 1.837 |
| EXAMPLE 3.2 | 48.0% | 2.416 | 2.131 | 1.000 | 204.6 | 1.415 |
| EXAMPLE 3.3 | 55.8% | 2.810 | 2.487 | 1.001 | 203.3 | 1.023 |
| EXAMPLE 3.4 | 64.0% | 3.209 | 2.842 | 1.000 | 203.2 | 0.603 |
| EXAMPLE 3.5 | 72.1% | 3.613 | 3.197 | 1.000 | 203.5 | 0.198 |

In all of the above studies, dilutions were performed using water as the diluent. However, fast evaporation of the diluent was suspected to be beneficial by providing less time for the catalytic destruction of the peracid by magnesium. Thus, diluents that evaporate more quickly were considered. Specifically, methanol (boiling point=64.7° C.), ethanol (78.4° C.), and isopropanol (82.6° C.) were tested in place of water as the diluent. Tests were performed using antimicrobial compositions of the following composition, and the overall measurement approach outlined in the main document above:

Antimicrobial solution=20 wt %
PEG 3350=20 wt %
$Mg(Ac)_2 \cdot 4H_2O$=4.1 wt %
Alcohol=55.9 wt %

Both room-temperature and 40° C. antimicrobial compositions were prepared. If success with the alcohols was higher than that with water, then additional alcohol studies were performed, including PEG-concentration, Mg-concentration, and antimicrobial solution-concentration studies.

Because modest success was found using $Mg(Ac)_2$ salts, and the peracid recovery using ethanol as a diluent instead of water was improved, accelerated-aging studies of antimicrobial compositions at high temperatures were performed. The antimicrobial compositions were prepared as follows:

Antimicrobial solution=20 wt %
PEG 3350=20 wt %
$Mg(Ac)_2 \cdot 4H_2O$=4.1 wt %
Diluent=55.9 wt %

Two diluents were tested, namely water and ethanol. Antimicrobial compositions were prepared as described in Example 2 above (20 μL into a glass HPLC vial), but only 40° C. drying was performed, and vials were placed in the oven immediately after the antimicrobial composition was added, to prevent long wait times at room temperature, while other vials were being prepared. All masses and oven-placement times were recorded. After at least 48 hr in a 40° C. oven, the vials were removed and weighed to begin the aging study. Date/time of removal from the 40° C. oven was recorded. Aging was performed at the following conditions: room temperature, room temperature (dry), 40° C., 55° C., 60° C., and 80° C. Using ASTM F1980-07 (see e.g. http://www.westpak.com/page/resources/accelerated-aging-time-calculator) to calculate aging, Table 3.2 provides the required times to claim a shelf life of 6 or 12 months assuming a 23° C. comparison temperature. For "room-temperature" aging, 21° C. was assumed for the laboratory test.

TABLE 3.2

Accelerated-aging Times Required for 6- or 12-Month Shelf-life Claims Assuming a 23° C. Shelf

| Desired Time | 21° C. | 40° C. | 55° C. | 60° C. | 80° C. |
|---|---|---|---|---|---|
| 6 Months | 210 | 57 | 20 | 14 | 3.5 |
| 12 Months | 419 | 113 | 40 | 29 | 7.0 |

The primary goal of the two room-temperature studies was to test the effect of relative humidity, as the ovens all operated at ambient absolute humidity, which was a quite low relative humidity at the temperatures of interest. Thus, the room-temperature/ambient humidity study was compared to the room-temperature/dry study as a control. The dry environment was attained using a desiccator. The testing schedule for the study was given as shown in Table 3.3. Note that this schedule was approximate.

TABLE 3.3

Testing Schedule for Antimicrobial Composition Vials at Various Temperatures, Given by Day Number from Start of Aging

|  | 21° C. | 40° C. | 55° C. | 60° C. | 80° C. |
|---|---|---|---|---|---|
| Vial 1 | 0 | 0 | 0 | 0 | 0 |
| Vial 2 | 7 | 7 | 3 | 3 | 2 |
| Vial 3 | 14 | 14 | 8 | 8 | 4 |
| Vial 4 | 28 | 21 | 14 | 14 | 7 |
| Vial 5 |  | 28 | 21 | 21 |  |
| Vial 6 |  |  | 30 | 29 |  |

One additional vial at each condition was prepared to serve as a backup or duplicate time point. Since two sets were prepared at 21° C., this meant 35 vials per antimicrobial composition and 70 vials total. Although a single t=0 point would suffice, a different t=0 point was used for each condition to serve as a six-fold replicate. No significant replicate testing of the application process had been performed to date, so this set of six served as a reproducibility measurement, in addition to precisely establishing the starting peracid levels. The samples at 80° C. were stored in a gas chromatography oven. To prevent the cooling fan from activating, which would cause large amounts of convection, the oven was turned off, instead of being set to a low temperature, for removal of a sample. After deactivation, the oven temperature took up to an hour to reach a temperature that was safe for handling. For the described aging study, mass measurements were only taken when applying the antimicrobial composition, at the start of the aging study, and when eluting the antimicrobial composition.

Example 3 Results

As shown in FIGS. 3 and 4, these antimicrobial compositions were also found to have acceptable lifetimes of six months or longer in accelerated-aging tests.

Example 4. Sterilization Testing of Coated Samples

The objective of this study was to investigate and determine if there was a quantifiable amount of peracid retained after sterilization. The sterilization methods were: gamma irradiation (G), ethylene oxide (EO) and electron beam (E-b).

In this study, two different formulations, with one containing magnesium acetate, PEG, ethanol and antimicrobial solution, and the other containing magnesium acetate, PEG, water and antimicrobial solution were utilized. These compositions were prepared per Example 2. The substrates on which the antimicrobial compositions were applied were HPLC screw thread caps with integral polypropylene membrane (Thermo Scientific National Vendor Catalog #C5000-50B). These substrates were pre-cleaned with 18 MΩ×cm water, and dried. The number of vials and/or caps needed for this work were summarized in Table 4.1. It was required to prepare enough samples so that some were kept in the lab at room temperature, as unsterilized controls, and another set was shipped to the sterilization company, but not processed. The latter set of control was necessary to evaluate the impact of shipping on the coated unsterilized samples. These controls were used for comparative purposes, versus the sterilized samples. To mimic the studies on the application of the antimicrobial composition, 20 µL were dispensed onto the substrates. The substrates were weighed pre- and post-addition of the antimicrobial composition. The masses were recorded to the nearest 0.01 mg. The coated substrates were dried in the oven at 40° C., for at least 24 hours and were kept at that temperature until ready to be shipped. The samples were allowed to cool to room temperature, and weighed, prior to placing in the sterilization pouch. The contents of each pouch were defined in Table 4.1. The samples were packaged in a configured box for sterilization, following the requirements of the sterilization company. Since there were three different sterilization methods under investigation, the packaging varied to comply with the requirements, per the sterilization technique.

Analytical testing by direct injection, as described in Example 2, to quantify the amount of peracid retained post-sterilization, was performed upon return of the samples. Samples for analysis, whether sterilized or unsterilized, were weighed prior to extraction. A comparative study of the sterilized samples was conducted, versus the unsterilized samples kept in-house and the returned unsterilized samples. The sterilization technique that resulted in either no loss, no substantial loss, or mere presence of measurable peracid amount, was considered the best suited method for SBI sterilization.

Two different antimicrobial compositions were prepared with the following composition:
Antimicrobial Composition 1 with Ethanol as Diluent (Identified as MgAcE):
Antimicrobial solution=20 wt. %
PEG 3350=20 wt. %
$Mg(Ac)_2 \cdot 4H_2O$=4.1 wt. %
Ethanol=55.9 wt. %
Antimicrobial Composition 2 with Water as Diluent (Identified as MgAcW):
Antimicrobial solution=20 wt. %
PEG 3350=20 wt. %
$Mg(Ac)_2 \cdot 4H_2O$=4.1 wt. %
Milli-Q Water=55.9 wt. %

TABLE 4.1

Number of samples required per sterilization method and type of antimicrobial solution

| | Sample ID | Sterilization Method | No. of Samples |
|---|---|---|---|
| EXAMPLE 4.1 | MgAcE-G | Gamma Irradiation | 12 |
| EXAMPLE 4.2 | MgAcE-EO | Ethylene Oxide | 12 |
| EXAMPLE 4.3 | MgAcE-E-b | E-beam Irradiation | 12 |
| EXAMPLE 4.4 | MgAcW-G | Gamma Irradiation | 12 |
| EXAMPLE 4.5 | MgAcW-EO | Ethylene Oxide | 12 |
| EXAMPLE 4.6 | MgAcW-E-b | E-beam Irradiation | 12 |
| EXAMPLE 4.7 | MgAcE-C | None (In-house Control) | 12 |

Example 4 Results

The antimicrobial compositions were shown to survive sterilization (separately) by gamma irradiation, ethylene oxide, and electron beams, and retain a quantifiable amount of peracid after the sterilization, as shown in FIG. 2.

Example 5. Humidity Sensitivity of Magnesium-Antimicrobial Solution-PEG Antimicrobial Compositions Storing and shipping the antimicrobial composition in an enclosed environment with a desiccant (silica gel or molecular sieves) was demonstrated to protect the peracid in the antimicrobial composition. This study evaluated the antimicrobial composition's sensitivity to humidity quantitatively, more specifically, it measured the humidity sensitivity of dry antimicrobial compositions prepared from solutions of 20 wt % antimicrobial solution/20 wt % PEG 3350/4.1 wt % magnesium acetate tetrahydrate/remainder water, in order to establish storage and transport conditions that are compatible with extended shelf lives (at least six months). The degradation of Mg-antimicrobial solution-PEG antimicrobial compositions of a defined formulation were tested, at room temperature, over a large relative humidity (RH) range. The peracid content of the antimicrobial composition at each condition was monitored for four weeks, to evaluate degradation rates at the various conditions. This was intended to gain a better understanding of the humidity sensitivity of the product, and provide guidance regarding proper storage conditions.

In order to test the antimicrobial compositions for humidity sensitivity, the antimicrobial compositions needed to be exposed to varying levels of humidity over time, and their peracid content needed to be monitored. Relative-humidity atmospheres above the antimicrobial compositions being tested were generated via the well-established approach of using saturated salt solutions to dictate the relative humidity in enclosed atmospheres containing the antimicrobial compositions of interest.

The sensitivity of the antimicrobial compositions to relative humidity (RH) were evaluated by exposing the antimicrobial compositions in question to a range of known RH values, and periodically sampling the antimicrobial compositions to measure peracid content and mass over several weeks. All testing was performed on samples stored at room temperature. Samples were initially dried at 40° C., and maintained there for three days, prior to desired RH/room temperature storage. The majority of the RHs were set using saturated salt solutions in a confined environment. Specific RHs ranged from 11.3% to 77.5%. Additional tests were performed in the presence of silica gel desiccant (very low RH), and pure water (100% RH). Both mass and chemical composition (peracid content) were measured over the course of four weeks. Specific details on the antimicrobial composition preparation, employed RHs, and analysis approach are given below.

Antimicrobial Composition Preparation

All antimicrobial compositions were prepared using a solution of the following composition:
20.0 wt % Antimicrobial solution (as described in Example 1)
20.0 wt % PEG 3350
4.1 wt % Magnesium acetate tetrahydrate
55.9 wt % Water Addition order was unimportant in antimicrobial composition preparation, except that the antimicrobial solution and magnesium components were not combined until the final step. Upon mixing and dissolution, the antimicrobial composition was used immediately. The time of antimicrobial composition preparation was recorded. Additional information on this antimicrobial composition can be found in Example 2.

Antimicrobial compositions were prepared by dispensing 20 µL of antimicrobial solution into an HPLC vial lid, and placing the lid into a 40° C. oven for drying. Masses of the dry lid and dispensed antimicrobial solution were recorded, as was the time the lid was placed into the oven. Antimicrobial compositions were not removed from the oven until after three days, at which time they were massed and transferred to their respective humidity "chamber." There were 11 different storage conditions (see Table 5.1), and 14 antimicrobial compositions prepared for each condition, combining for 154 total antimicrobial composition preparations. Because of the time required to prepare so many antimicrobial compositions, this preparation was divided up between two (ideally) identical antimicrobial solutions, to help prevent significant effects due to solution age. Also, to help prevent biasing from age, the various conditions' samples were prepared in parallel, instead of in series (i.e. all of the "#1" samples were prepared back-to-back, instead of all of a single salt, followed by all of another salt). Finally, the lids were prepared in the followed order as a way to randomize the sampling to avoid biasing:

Solution 1, lid order: 6, 14, 2, 12, 10, 8, 4
Solution 2, lid order: 7, 9, 11, 1, 13, 5, 3

These combined efforts were designed to ensure that any antimicrobial composition-age influences would be minimal. Note: for nomenclature convention, each lid was identified via abbreviation for its establishment method (see Table 5.1 below), followed by the number of that sample. Also, note that because 77 samples from each solution were prepared, equating to 1.54 mL, no more than 5 mL of each antimicrobial solution needed to be prepared.

Relative humidity of the headspace above the antimicrobial compositions was established by keeping the antimicrobial compositions in an enclosed environment, in the presence of a saturated salt solution that provided a known relative humidity. The relative humidity conditions (assuming 21° C.), and how they will be attained, were compiled in Table 5.1.

TABLE 5.1

Relative Humidity, Method of Attaining Target Humidity, and Solubility of Salt (if applicable) for Testing

| Relative Humidity | Establishment Method | Salt Solubility |
|---|---|---|
| Low | Silica gel | — |
| 11.3% | Lithium chloride | 84 g/100 mL (45.8 wt %) |
| 18.1% | Calcium bromide (hydrate) | 143 g/100 mL |
| 23.0% | Potassium acetate | 269 g/100 mL |
| 33.0% | Magnesium chloride | 167 g/100 mL |
| ~33% | Calcium chloride (dihydrate) | 134.5 g/100 mL (at 60° C.) |
| 43.2% | Potassium carbonate | 112 g/100 mL |
| 54.1% | Magnesium nitrate (hexahydrate) | 125 g/100 mL |
| 58.8% | Sodium bromide | 94.3 g/100 mL |
| 75.5% | Sodium chloride | 35.9 g/100 mL |
| 100% | Water | — |

The saturated salt solutions were prepared at least two days in advance, to ensure practically complete equilibrium. They were prepared in glass scintillation vials, using at least 5 mL of solution, and visually inspected to ensure solid remained in the vial. All salt and water masses used to generate these solutions were recorded. Care was taken, as preparation of high-concentration salt solutions could induce large changes in solution temperature. The silica gel samples were stored in a research lab desiccator, with several packets of silica gel. The remaining samples were stored in small, portable desiccators (Fisher Scientific part number 08-664-5A, or equivalent). Because these desiccators lacked a means of tightening the lid, and ensuring an airtight seal around the O-ring, an additional weight (such as a metal block) was placed on top of the lid, and the desiccator itself was stored inside of a gallon-sized storage bag, in order to increase mass-transfer resistance between the desiccated region and ambient atmosphere. Calcium chloride was selected for testing because it is a common, low-cost commercial desiccant that can be used in place of silica gel, for shipping and storage.

The desiccators were only opened to ambient atmosphere during a sampling event. For each sampling event, two coated lids were removed from each desiccator, extracted, and analyzed by direct-injection HPLC analysis. The extraction eluent (a low-pH phosphate buffer) and HPLC mobile phase/method are described in Example 2. Both coated lid mass, and extraction eluent mass, were recorded. Extractions took place for at least 3 min, and HPLC analysis of an extract began within 90 min of the extraction start. In addition to the lids being extracted, both the #13 and #14 lids were massed, and returned to the desiccator, for each sampling event. This increased the number of mass measurements made throughout the experiment, to improve the statistics on the deliquescence-point evaluation. The amount of time that the #13 and #14 lids were out of the desiccator, was kept to a minimum, and the same was true for the amount of time the desiccator lid was removed.

Coated lids were placed into their respective desiccators on Day 0. The first time points were obtained on Day 3, and a Monday/Thursday sampling schedule was maintained beginning that day, with the final sampling day being pushed back due to scheduling conflicts. The full sampling schedule was recorded in Table 5.2. Note that 22 antimicrobial composition extracts, plus one antimicrobial solution standard, were analyzed, per analysis day. If one RH value yielded no peracid for both samples, two dates in a row, and the RH value immediately below it also showed no peracid on those dates, then only masses and not HPLC analyses were performed for RH samples for subsequent dates. Similarly, if an RH value yielded no measurable peracid in either sample for three sequential dates, no further HPLC analyses on it were performed.

TABLE 5.2

Sampling Schedule for Extractions

| Day # | Lid #'s |
|---|---|
| 3 | 1-2 |
| 6 | 3-4 |
| 10 | 5-6 |
| 13 | 7-8 |
| 17 | 9-10 |
| 20 | 11-12 |
| 27 | 13-14 |

Example 5 Results

Results showed that everything stored with potassium carbonate (RH=43%) or at higher RH failed. Storage with calcium chloride succeeded, whereas storage with magnesium chloride failed, and both of these should have deliquescence points near 33%. Storage with potassium acetate (RH=23%) and everything of lower RH succeeded. Thus, the deliquescence point of the material was believed to be close to 33%.

Example 6. Solid-Phase Antimicrobial Composition Powder and Tablet Synthesis and Testing Several solid-phase antimicrobial composition powders were prepared using lyophilization. Four syntheses were done successfully, yielding solids designated "F-1", "F-2", "F-3", and "NoMeOH". The synthesis results for F-1, F-2 and F-3 were summarized in Table 6.1. NoMeOH was prepared similarly to F-1, but with no methanol added.

TABLE 6.1

Properties of Solid Antimicrobial Composition

| Parameters | F-1 | F-2 | F-3 |
|---|---|---|---|
| Appearance | White crystals | White granules | White granules |
| Flowability | Poor | Moderate | Better |
| Wt. recovered | 1.22 g | 2.13 g | 0.36 g |
| Peracetic acid content (% over solid) | 2.4% | 0.55% | 0.92% |
| % Retention | 34% | 14% | 3.9% |
| Antimicrobial efficacy | Yes | | |

NoMeOH was prepared similarly to F-1, but with no methanol added. The NoMeOH was found to contain 2.7 wt % peracetic acid.

F-1 antimicrobial composition powders were mix with other functional ingredients such as a bulking agent, glidant, effervescent agent and disintegrating agent, and compressed into a tablet form.

Procedure: The required weight of antimicrobial composition powder and excipients, as described in Tables 6.2 and 6.3, were transferred into a mortar. The weight of the mortar was recorded. The contents of the mortar were mixed, using a pestle, for 15 minutes, after which they were checked for uniformity and flowability. About 1 g of the powder was poured into either a mold or a single punch tablet machine, and pressed, making tablets. The weight of each tablet was checked, and determined to be approximately 1.0±0.1 g. One table was characterized for effervescent effect (see Table 6.4) and found to have an effervescent time of 3 minutes. The tablet completely dissolved, and the resulting solution was clear and free of visual particulates.

TABLE 6.2

Compositions (% w/w)

| Components | % w/w |
|---|---|
| F-1 Solid Antimicrobial Composition (2.4%) | 41.6 |
| Mannitol | 12.4 |
| Citric acid | 25 |
| Sodium bicarbonate | 20 |
| Magnesium stearate | 1 |

TABLE 6.3

Dispensing (g/10 g)

| Components | g/10 g |
|---|---|
| F-1 Solid Antimicrobial Composition (2.4%) | 4.16 |
| Mannitol | 1.24 |
| Citric acid | 2.5 |
| Sodium bicarbonate | 2 |
| Magnesium stearate (lubricant) | 0.1 |

TABLE 6.4

Properties of Antimicrobial Composition Tablet

| Appearance | Off-white |
|---|---|
| Hardness | 9.2 K.P (kilopond) |
| Effervescent time | 3 minutes |
| Tablet weight | 1 g |
| Intended peracetic acid | 10 mg/tablet |

Example 7. Efficacy of Solid-Phase Antimicrobial Composition

Two lyophilized-powder samples ("F-1" and "NoMeOH") were tested for antimicrobial activity against *Pseudomonas aeruginosa* and *Staphylococcus aureus*. Samples were dissolved/reconstituted in water to make a liquid biocide for liquid-suspension tests. NoMeOH was diluted to peracetic acid concentrations of 20 ppm and 200 ppm. F-1 was diluted to peracetic acid concentrations of 20 ppm and 158 ppm

*Pseudomonas aeruginosa* and *Staphylococcus aureus* were streaked to agar plates, and grown aerobically overnight at 36±2° C. Suspensions of the *Pseudomonas aeruginosa* and *Staphylococcus aureus* cultures were prepared to a 0.5 McFarland turbidity. Each culture was diluted to a theoretical concentration of $5 \times 10^4$ cfu/mL and 50 μL was spiral plated onto the appropriate agar plate. The culture suspensions were incubated aerobically overnight at 36±2° C. The suspension was further diluted to $5 \times 10^3$ cfu/mL in diluent, and used for the organism suspension in the Tests A, B, C and D, described below. The disinfectant was prepared by adding sterile distilled water (45 mL) and 10.8% antimicrobial composition (83 μL) and mixed well.

Test A: 50 μL of the organism suspension was diluted into 4.5 mL Dey-Engley Neutralizing Broth (D/E), to obtain a theoretical concentration of 30-100 cfu/mL. 0.5 mL of the antimicrobial composition was added to the D/E and allowed to sit for ≥5 minutes. Duplicate 0.1 mL aliquots were surface plated onto the appropriate agar, and incubated aerobically until growth was sufficient to count. Test A was performed three times.

Test B: 50 μL of the organism suspension was diluted into 4.5 mL D/E, to obtain a theoretical concentration of 30-100 cfu/mL. 0.5 mL of diluent was added to the D/E and allowed to sit for ≥5 minutes. Duplicate 0.1 mL aliquots were surface plated onto the appropriate agar, and incubated aerobically until growth was sufficient to count. Test B was performed three times.

Test C: 50 μL of the organism suspension was diluted into 5 mL diluent, to obtain a theoretical concentration of 30-100 cfu/mL, and allowed to sit for ≥5 minutes. Duplicate 0.1 mL aliquots were surface plated onto BA, and incubated anaerobically at 36±2° C. overnight. Test C was performed three times.

Test D: 50 μL of the organism suspension was diluted into 5 mL antimicrobial composition, to obtain a theoretical concentration of 30-100 cfu/mL, and allowed to sit for ≥5 minutes. Duplicate 0.1 mL aliquots were surface plated onto the appropriate agar, and incubated aerobically until growth was sufficient to count. Test D was performed three times.

Two other test articles were used, namely a negative control and a positive control:

Negative control: magnesium acetate tetrahydrate, present at concentrations equivalent to the dissolved solids for the 20- and 200-ppm tests of no MeOH.

Positive control: antimicrobial composition liquid concentrate diluted to 20 ppm and 200 ppm.

Example 7 Results

*Pseudomonas Aeruginosa* Results ($Log_{10}$ Kills)
20 ppm antimicrobial composition: ≥6.1
200 ppm antimicrobial composition: ≥6.1
20 ppm F-1: ≥6.1
158 ppm F-1: ≥6.1
20 ppm NoMeOH: ≥6.1
200 ppm NoMeOH: ≥6.1
"Low" Magnesium Acetate (equivalent to 20 ppm samples): 0.1
"High" Magnesium Acetate (equivalent to 200 ppm samples): 0.0

*Staphylococcus Aureus* Results ($Log_{10}$ Kills)
20 ppm antimicrobial composition: 1.3
200 ppm antimicrobial composition: ≥6.2
20 ppm F-1: 0.3
158 ppm F-1: ≥6.2
20 ppm NoMeOH: 0.5
200 ppm NoMeOH: ≥6.2
"Low" Magnesium Acetate (equivalent to 20 ppm samples): 0.0
"High" Magnesium Acetate (equivalent to 200 ppm samples): 0.0

Overall, the solid-phase maintained nearly all of the antimicrobial efficacy of the liquid-phase antimicrobial composition.

The invention claimed is:

1. An article configured for tissue contact, comprising a surface coated with an antimicrobial composition consisting of a dried solid-phase peracetic acid metal salt precipitate, wherein said metal salt precipitate is a reaction product of a mixture consisting of the polymer matrix support, hydrogen peroxide, peracetic acid, acetic acid and a basic metal salt selected from the group consisting of magnesium, zinc and lithium metal salts, wherein the basic metal salt is present in an amount effective to adjust the composition pH to between 3.5 and 7.5, and
the antimicrobial composition coating has a thickness of at least 10 μm.

2. The article according to claim 1, wherein the acetic acid concentration in the mixture is 2.75 M.

3. The article according to claim 1, wherein the basic metal salt is in a molar ratio to peracetic acid in the mixture from about 0.1:1 to about 10:1.

4. The article according to claim 1, wherein the amount of peracetic acid in the mixture is from 0.1% to 85%.

5. The article according to claim 1, wherein the basic metal salt is selected from the group consisting of a carbonate, hydroxide, oxide, acetate or formate metal salt, or a metal salt of an organic acid corresponding to the reduced form of the peracetic acid.

6. The article according to claim 1, wherein the article is an implant.

7. The article according to claim 6, wherein the implant is bioabsorbable.

8. The article according to claim 1, wherein the surface is coated with a second coating, and the antimicrobial composition coating is applied on top of the second coating.

9. The article according to claim 1, wherein the polymer matrix support is a polyethylene glycol.

* * * * *

UNITED STATES PATENT AND TRADEMARK OFFICE
CERTIFICATE OF CORRECTION

| | | |
|---|---|---|
| PATENT NO. | : 12,232,962 B2 | Page 1 of 1 |
| APPLICATION NO. | : 16/780581 | |
| DATED | : February 25, 2025 | |
| INVENTOR(S) | : Scott Noblitt | |

It is certified that error appears in the above-identified patent and that said Letters Patent is hereby corrected as shown below:

In the Claims

Column 32, Lines 17-28, Claim 1, should read as follows:
1. An article configured for tissue contact, comprising a polymer matrix support coated with an antimicrobial composition consisting of a dried solid-phase peracetic acid metal salt precipitate, wherein said metal salt precipitate on the polymer matrix support is a reaction product of a mixture consisting of hydrogen peroxide, peracetic acid, acetic acid and a basic metal salt selected from the group consisting of magnesium, zinc and lithium metal salts, wherein the basic metal salt is present in an amount effective to adjust the composition pH to between 3.5 and 7.5, and
the antimicrobial composition coating has a thickness of at least 10 μm.

Signed and Sealed this
First Day of April, 2025

Coke Morgan Stewart
*Acting Director of the United States Patent and Trademark Office*